United States Patent

Chibata et al.

[11] 4,032,641
[45] June 28, 1977

[54] NICOTINOYL CARNITINE DERIVATIVES

[75] Inventors: Ichiro Chibata, Suita; Munetsugu Miyoshi, Nishinomiya; Kohki Takashima, Shiki; Shoji Moriya, Takarazuka, all of Japan

[73] Assignee: Tanabe Seiyaku Co., Ltd., Osaka, Japan

[22] Filed: June 9, 1976

[21] Appl. No.: 694,363

[52] U.S. Cl. .................. 424/266; 260/295.5 R; 260/295.5 A
[51] Int. Cl.² ............ A61K 31/455; C07D 213/55; C07D 213/56
[58] Field of Search ............ 260/295.5 R, 295.5 A; 424/266

[56] References Cited

UNITED STATES PATENTS 3,337,569  8/1967  Imhoff .................. 260/295.5 A

FOREIGN PATENTS OR APPLICATIONS 2,162,334  7/1973  France .................. 260/295.5 A

*Primary Examiner*—Alan L. Rotman
*Attorney, Agent, or Firm*—Jordan B. Bierman; Linda G. Bierman

[57] ABSTRACT

A nicotinoyl carnitine compound of the formula:

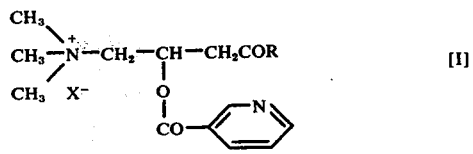

[I]

wherein R is lower alkoxy, benzyloxy or amino and X is an anionic residue of a pharmaceutically acceptable acid, is prepared by reacting a carnitine derivative of the formula:

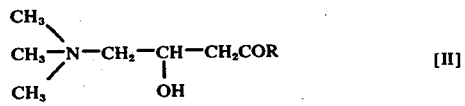

[II]

wherein R is the same as defined above, with nicotinic acid or a functional derivative thereof. The derivative [I] and the pharmaceutically acceptable acid addition salts of said compound are useful as hypolipidemic agents.

13 Claims, No Drawings

NICOTINOYL CARNITINE DERIVATIVES

This invention relates to a novel nicotinoyl carnitine compound and a process for preparing the same. More particularly, it relates to a compound of the formula:

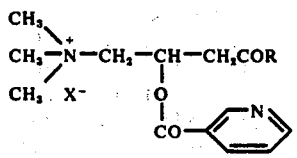  [I]

wherein R is lower alkoxy, benzyloxy or amino and X is an anionic residue of a pharmaceutically acceptable acid, or a pharmaceutically acceptable acid addition salt of said compound.

It is known that cholesterol and triglyceride levels in plasma can be decreased by the use of nicotinic acid [Clin. Med. 82 (7), 19 – 26(1975); Atherosclerosis 18(1), 1 – 9(1973)]. However, the use of nicotinic acid as a hypolipidemic agent possesses undesirable side effects such as facial skin flush and itching. On the other hand, carnitine, normally present in the body, enzymatically combines with fatty acids to facilitate their transport through the mitochondrial membranes and is an important factor in metabolism of fatty acids [Pharmacological Society 56(6), page 798(1970)]. In this connection, Japanese patent application No. b 530044/1973(laid open to the public without examination under No. 47519/1974) discloses that carnitine, when used in combination with a lipolytic agent, is useful in treating the obesity of mammals. Additionally, the synthesis of several carnitine esters has been reported recently. For example, the synthesis of carnitine alkyl esters, O-linoleyl carnitine chloride and carnitine, have been disclosed in Chemical Abstracts 64(1966), 19398g, Japanese patent publication No. 24006/1972 and Japanese patent publication No. 24/1963, respectively.

During the course of various investigations, we have now succeeded in the synthesis of a novel carnitine ester, i.e., o-nicotinoyl carnitine compound, and at the same time found that it is useful as a hypolipidemic agent. The nicotinoyl carnitine compound [I] of the present invention exhibits a potent hypotriglyceridemic and hypocholesterolemic activity, and the activity of the compound [I] lasts longer than that of nicotinic acid. Further, it has a remarkably low toxicity and does not show side effects such as facial skin flushing, itching, etc. to any substantial degree. The nicotinoyl carnitine derivative [I] may be therefore useful in treating or preventing arteriosclerosis, cardiac infarction, stenocardia, cerebral hemorrhage, softening of the brain, hypercholesteremia and/or lipemia.

The nicotinoyl carnitine compound [I] can be used as a pharmaceutical agent either in the form of a pharmaceutically acceptable acid addition salt of said compound or without converting it to said salt. The pharmaceutically acceptable acid addition salts derived from the nicotinoyl carnitine compound [I] include the hydrochloride, hydrobromide, nitrate, sulfate, phosphate, chlorate, bromate, acetate, propionate, valerate, malonate, succinate, methanesulfonate, ethanesulfonate, benzenesulfonate, toluenesulfonate and so forth.

Further, the nicotinoyl carnitine compound [I] can be used either alone or in combination with a pharmaceutical excipient which is suitable for oral or parenteral administration. The excipient selected should be one which does not react with the compound. Suitable excipients include gelatin, lactose, glucose, cellulose, carboxymethylcellulose, anhydrous silicic acid, aluminium silicate, dextrin, starch, magnesium stearate, talcum and vegetable oils. The nicotinoyl carnitine compound may be administered to patients either orally or parenterally. For oral administration, solid dosage forms such as capsules and coated or uncoated tablets may be utilized. On the other hand, liquid dosage forms such as a solution and an emulsion may be used for parenteral administration. The pharmaceutical preparation may be sterilized and/or may contain auxiliaries such as preserving, stabilizing or emulsifying agents. When administered orally, the preferred daily dose for an adult patient is about 200 mg to about 10 g, especially about 300 mg to about one g. However, the precise effective dose of the compound as a hypolipidemic agent may vary depending on the mode of administration and conditions to be treated.

According to the present invention, the nicotinoyl carnitine compound [I] can be prepared by reacting a carnitine compound of the formula:

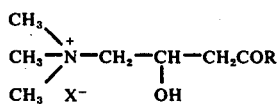  [II]

with nicotinic acid or a functional derivative thereof.

The starting compound [II] may be prepared by conventional esterification or amidation of carnitine. The compound [II] may also be prepared by alcoholysis and/or partial hydrolysis of a cyano compound having the formula:

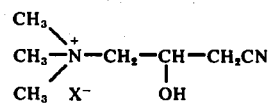

In the above-mentioned compounds [I] and [II], the preferred examples of the lower alkoxy group represented by the symbol R include methoxy, ethoxy, propoxy, butoxy and the like. The group X includes the anionic residues of various pharmaceutically acceptable acids such as mineral acids, organic mono- or dicarboxylic acids, organic sulfonic acids and so forth. More specifically, the group X may include halide ions (e.g., chloride, bromide ions), nitrate ion, sulfate ion, chlorate ion, bromate ion, lower alkane-monocarboxylate ions (e.g., acetate, propionate, valerate ions), lower alkane-dicarboxylate ions(e.g., malonate, succinate ions), lower alkene-dicarboxylate ions(e.g., fumarate, maleate ions), lower alkyl sulfonate ions (e.g., methanesulfonate, ethanesulfonate ions), and substituted or unsubstituted phenylsulfonate ions (e.g., benzenesulfonate, toluenesulfonate ions). Further, examples of the functional derivative of nicotinic acid which are suitable for use in the present invention include nicotinic anhydride, nicotinoyl halide (e.g., chloride, bromide), mixed acid anhydrides (e.g., nicotinoyl ethylcarbonate, nicotinic trichloroacetic anhydride, nicotinic benzenesulfonic anhydride), and nicotinic acid esters (e.g., N-hydroxysuccinimide, N-hydroxybenztriazol or cyanomethyl esters of nicotinic acid).

When the functional derivative of nicotinic acid is employed as one of the starting materials of the present invention, the reaction thereof with the compound [II] is preferably carried out in the presence of an acid acceptor. Tertiary amines (e.g., triethylamine, trimethylamine, N-methylpyperidine, quinuclidine, N,N-dimethylaniline), nitrogen-containing unsaturated heterocyclic compounds (e.g., pyridine, picoline, quinoline), alkali metal salts or ogranic carboxylic acids (e.g., sodium acetate, sodium benzoate), alkali metal hydroxides (e.g., sodium hydroxide), alkali metal carbonates (e.g., sodium carbonate) and other suitable organic or inorganic bases may be employed as the acid acceptor. On the other hand, when nicotinic acid per se is employed in the invention, the reaction thereof with the compound [II] is carried out in the presence of a dehydrating agent. Dicyclohexylcarbodiimide, carbonyldiimidazol and the like are suitable as the dehydrating agent.

The above-mentioned reactions of the present invention can be conducted with or without a solvent. Further, the temperature at which the above-mentioned reactions are performed is not critical in the present invention. Generally, however, it is preferred to carry them out at a temperature of −10° to 70° C. Preferred examples of the reaction solvent include dimethylformamide, dimethylsulfoxide, pyridine, chloroform, acetone, acetonitrile, ethylacetate, tetrahydrofuran and dioxane.

The acid addition salt of the nicotinoyl carnitine compound [I] of the present invention can be prepared by treating the compound with at least one molar equivalent of a pharmaceutically acceptable acid. The acid addition salt may also be prepared by treating the compound with about one molar equivalent of a conventional acid such as hydrohalic acid and then converting the resultant hydrohalide into a desired salt by conventional methods. In both of the cases, the reaction is preferably conducted in water and/or an organic solvent at a temperature of about 0° to about 60° C, especially at room temperature. Methanol, ethanol, acetone, acetonitrile and so forth are suitable as the organic solvent.

Practical and preferred embodiments of the present invention are shown in the following examples. In this Specification and Claims, each one of the terms "lower alkoxy", "lower alkyl", "lower alkane" and "lower alkene" should be interpreted as referring to compounds having one to five carbon atoms. Further, the electrophoresis were carried out by placing samples on Toyo's filter paper No. 51A moistened with a mixture of water, acetic acid, and pyridine (89 : 10 : 1) having a pH of 3.6, placing the ends of the paper in an electric vessel containing the same solvent as mentioned above, and passing an electric current of 2000 volts through the paper for one hour. Then, the relative electrophoretic mobility values (i.e., Rm-values) of each sample was estimated [Standard compound: carnitine amide chloride (Rm = 1.00)].

EXAMPLE 1

11.3 g of carnitine ethyl ester chloride are dissolved in 60 ml of chloroform. 13.7 g of nicotinic anhydride are added to the solution under water-cooling and stirring. 6.1 g of triethylamine are added dropwise to the mixture at a temperature below 10° C. The mixture is stirred at room temperature for 2 hours, cooled to below 10° C and then 7.5 g of dioxane-hydrochloric acid (HCl-content: 29%) are added dropwise thereto. The mixture is further stirred at the same temperature for one hour, and the crystalline precipitates are removed by filtration. The filtrate is concentrated under reduced pressure. After 45 ml of acetone are added to the residue, this mixture is cooled to below 10° C. The mixture is filtered to remove the crystalline precipitates, and the precipitates are washed with 10 ml of acetone. The combined filtrate and washing are concentrated under reduced pressure. 20 ml of acetone and 0.9 ml of water are added to the oily residue obtained, and the mixture is allowed to stand overnight in a refrigerator. The crystalline precipitate thus obtained are collected by filtration and recrystallized from 50 ml of acetone-water (water-content: 0.9 ml). 15.0 g of nicotinoyl carnitine ethyl ester chloride.H$_2$O are obtained as colorless prisms. M.p. b 86° − 88° C. Yield: 86%

Rm-value: −0.76

Thin layer chromatography:

Rf-value: 0.56 [Silica gel plate, Solvent: chloroform -methanol-water-isopropanol-acetic acid (60 : 40 : 15 : 10 : 10)]

EXAMPLE 2

10.6 g of carnitine methyl ester chloride are dissolved in 60 ml of chloroform. 13.7 g of nicotinic anhydride are added to the solution under ice-cooling and stirring. 6.1 g of triethylamine are added dropwise to the mixture at a temperature below 10° C. After said dropwise addition, the mixture is stirred at room temperature for 2 hours. Then, the mixture is treated in the same manner as described in Example 1. 12 g of nicotinoyl carnitine methyl ester chloride are obtained as colorless prisms. M.p. 144° − 146° C(recrystallized from methanol-ethylacetate). Yield: 76%

EXAMPLE 3

4.1 g of potassium nicotinate are suspended in 50 ml of chloroform. 3 g of thionyl chloride are added dropwise to the suspension under stirring. The suspension is stirred at room temperature for one hour and then at 50° C for 3 hours. After cooling, the suspension is added dropwise to 50 ml of a chloroform suspension containing 5.28 g of carnitine methyl ester chloride and 5 g of triethylamine. Said dropwise addition is carried out under ice-cooling and stirring. After triethylamine is further added to the mixture so as to keep it at an alkaline pH, said mixture is stirred at room temperature for 24 hours. The mixture is filtered to remove the precipitates. The filtrate is adjusted to pH 3 with chloroform-hydrochloric acid and allowed to stand at room temperature overnight. Then, the precipitates are again removed by filtration. The filtrate thus obtained is concentrated, and to the residue is added ethylacetate. The resultant crystalline precipitates are collected by filtration and then recrystallized from methanol-ethylacetate. 4.5 g of nicotinoyl carnitine methyl ester chloride are obtained as colorless prisms. M.p. 144° − 146° C. Yield: 57%

EXAMPLE 4

A solution of 123 g of nicotinic acid and 140 ml of triethylamine in 600 ml of chloroform is cooled to −5° to −10° C. 110 g of ethyl chlorocarbonate are added to the solution under stirring. Then, the solution is stirred at the same temperature for 30 minutes. To the nicotinoyl ethylcarbonate solution obtained are added 115 g of carnitine ethyl ester chloride. The mixture is stirred at room temperature overnight, concentrated under reduced pressure and then filtered to remove the precipitates. The precipitates are washed with chloroform. The combined filtrate and washings are concentrated under reduced pressure. 600 ml of acetone are added to the residue. The precipitates are again removed by filtration, and the filtrate obtained is concentrated under reduced pressure. The oily residue thus obtained is washed with petroleum ether benzene (4 : 1). Then, 250 ml of acetone containing 9 ml of water are added to the oily reside, and the mixture is allowed to stand overnight in a refrigerator. The resultant crystalline precipitates are collected by filtration and then recrystallized from 330 ml of acetone - water (water-content: 3.3 ml). 134 g of nicotinoyl carnitine ethyl ester chloride.$H_2O$ are obtained as colorless prisms. M.p. 86° – 88° C. Yield: 77%

EXAMPLE 5

5.76 g of carnitine benzyl ester chloride and 5.5 g of nicotinic anhydride are suspended in 30 ml of chloroform. 3.4 ml of triethylamine are added dropwise to the suspension at a temperature below 10° C under stirring. After said dropwise addition, the mixture is stirred at room temperature for 3 hours. Then, the mixture is treated in the same manner as described in Example 1. 6.2 g of nicotinoyl carnitine benzyl ester chloride are obtained as colorless prisms. M.p. 166° – 168° C.
  Yield: 80%
  Rm-value: −0.72
  Thin layer chromatography: Rf-value: 0.66 [Silica gel plate, Solvent: chloroform -methanol-water-isopropanol-acetic acid (60 : 40 : 15 : 10 : 10)]

EXAMPLE 6

A solution of 17.6 g of nicotinic acid and 15.2 g of triethylamine in 110 ml of chloroform is cooled to −5° to −10° C, and 16.2 g of ethyl chloroformate are added dropwise thereto under stirring. The solution is stirred at the same temperature for 30 minutes. After 18.0 g of carnitine ethyl ester chloride are added to the nicotinoyl ethylcarbonate solution obtained above, the solution is further stirred at room temperature overnight. Then, the solution is evaporated to remove solvent, 20 ml of acetonitrile is added to the residue, and the mixture is filtered to remove the precipitates. The precipitates are washed with 20 ml of acetonitrile. The combined filtrate and washings are concentrated under reduced pressure. The residue is dissolved in one liter of water. The aqueous solution is passed through the column of 600 ml of an ion exchange resin [Amberlite IRA-400($NO_3$form)]. The column is washed with water. Then, the eluate and washings are combined and concentrated. The residue thus obtained is dissolved in 150 ml of acetone. 5.31 ml of 60% nitric acid are added to the acetone solution and, after cooling, the crystalline precipitates are collected by filtration and recrystallized from ethanol. 19.3 g of nicotinoyl carnitine ethyl ester nitrate.$HNO_3$ are obtained as colorless needles. M.p. 160° – 160° C. (decomp.)
  Yield: 57.5%
  Rm-value: −0.76
  Thin layer chromatography: Rf-value: 0.56 [Silica gel plate, Solvent: chloroform -methanol-water-isopropanol-acetic acid (60 : 40 : 15 : 10 : 10)]

EXAMPLE 7

A solution of 34.9 g of nicotinoyl carnitine ethyl ester chloride monohydrate in 1500 ml of water is passed through the column of 600 ml of an ion exchange resin [Amberlite IRA-400($PO_3$-form)]. The column is washed with one liter of water. The combined eluate and wash water is concentrated under reduced pressure. 150 ml of isopropanol are added to the residue. Then, the crystalline precipitates are collected by filtration and recrystallized from ethanol-acetone. 32.4 g of nicotinoyl carnitine ethyl ester phosphate are obtained as colorless needles. M.p. 109° – 110° C. (decomp.)
  Yield: 82.6%

EXAMPLE 8

59.4 g of carnitine chloride are suspended in 300 ml of isobutanol, and 49.5 g of thionyl chloride are added dropwise thereto at 10° to 15° C. The mixture is stirred at 25° to 30° C for 2 days. After the reaction, the mixture is filtered to remove insoluble materials, and the filtrate is concentrated at a temperature below 40° C. 50 ml of isobutanol are added to the residue, and the mixture is again concentrated in the same manner as above (these operations are repeated 3 times). Then, 200 ml of a mixture of isopropyl ether and acetone (5 : 1) is added to the residue. The crystalline precipitates are collected by filtration, washed with 50 ml of isopropyl ether, and dried. 38 g of carnitine isobutyl ester chloride are obtained. M.p. 89° – 91° C. Yield: 50%

5.08 g of carnitine isobutyl ester chloride are dissolved in 30 ml of chloroform. 5.71 g of nicotinic anhydride and 0.1 g of triethylamine are added to the solution, and the mixture is stirred at room temperature for 20 hours. After insoluble materials are removed by filtration, the filtrate is concentrated. The oily residue is washed with 30 ml of a mixture of ethyl ether and acetone (3 : 1), and the washing is removed by decantation (these operations are repeated 3 times). The residue thus obtained is dried under reduced pressure. 3.80 g of nicotinoyl carnitine isobutyl ester chloride are obtained. OiL. Rm-value: −0.72
  Thin layer chromatography: Rf-value: 0.68 [Silica gel plate, Solvent: chloroform -methanol-water-isopropanol-acetic acid(60 : 40 : 15 : 10 : 10)]

EXAMPLE 9

21 g of carnitine amide chloride and 30 g of nicotinic anhydride are added to a mixture of 65 ml of dimethylformamide and 10.8 g of triethylamine. The mixture is stirred vigorously at 60° – 70° C for one hour. After the reaction, the mixture is evaporated under reduced pressure to remove solvent. 200 ml of ice-water are added to the residue, and the aqueous mixture is filtered to remove the precipitates. The precipitates are washed with water. The combined filtrate and washings are washed with ethylacetate 2 times repeatedly. The aqueous layer is treated with activated charcoal and concentrated under reduced pressure. The residue is dissolved in ethanol. Then, the ethanol solution is again concentrated to remove solvent. n-Propanol is added to the residue thus obtained, and the mixture is allowed to stand in a refrigerator. The resultant crystalline precipitates are collected by filtration and then recrystallized from ethanol-n-propanol. 20.3 g of nicotinoyl carnitine amide chloride are obtained as colorless prisms. M.p. 185° – 187° C. Yield: 63%

EXAMPLE 10

21 g of carnitine amide chloride and 30 g of nicotinic anhydride are added to a mixture of 65 ml of dimethylformamide and 10.8 g of triethylamine. The mixture is heated gradually until the temperature reaches to 60°–70° C, and then stirred vigorously at the same temperature for one hour. After the reaction, the mixture is evapoated under reduced pressure to remove solvent. 200 ml of ice-water are added to the residue, and the aqueous mixture is filtered to remove the precipitates. The precipitates are washed with water. The combined filtrate and washing is washed with ethylacetate 2 times repeatedly. After treatment with activated charcoal, the aqueous layer is passed through the column of an ion exchange resin [Amberlite IRA-400 (acetic acid-form)]. The column is washed with water. The combined eluate and washing are treated with activated charcoal and then concentrated at 50° C under reduced pressure. Nicotinoyl carnitine amide acetate is thereby obtained as crude crystals. The crude crystals are dissolved in ethanol, and the ethanol solution is concentrated under reduced pressure (these operations are repeated twice). The residue is dissolved in 200 ml of ethanol. 85.7 g of ethanol-hydrochloric acid (HCl-content: 10%) are added to the solution. Then, the mixture is concentrated under reduced pressure. The residue obtained is again dissolved in 100 ml of ethanol, and the ethanol solution is concentrated. The residue thus obtained is dissolved in 100 ml of ethanol under heating. After cooling, the crystalline precipitates are collected by filtration, washed with ethanol and then recrystallized from methanol-acetone. 27.0 g of nicotinoyl carnitine amide chloride.HCl are obtained as colorless pillar crystals. M.p. 180°–181° C. Yield: 73%

EXAMPLE 11

43 g of carnitine amide chloride are dissolved in 500 ml of water. The solution is passed through the column of 650 ml of an ion exchange resin [Amberlite IRA-400(acetic acid-form)]. The column is washed with one liter of water. The combined eluate and washing are concentrated. The residue obtained is dissolved in 200 ml of dimethylformamide, and the solution is evaporated to remove solvent (these operations are repeated once more). Carnitine amide acetate is thereby obtained as a pale yellow oil. Carnitine amide acetate is dissolved in 500 ml of dimethylformamide, and 60 ml of pyridine are added thereto. Then, 75 g of nicotinic anhydride are added to the solution at room temperature under stirring. The mixture is stirred at room temperature for 15 hours. After the reaction, the mixture is evaporated under reduced pressure to remove the solvent. 500 ml of water are added to the residue, and the aqueous mixture is filtered to remove the precipitates. The precipitates are washed with water. The combined filtrate and washing are passed through the column of 650 ml of an ion exchange resin [Amberlite IRA-400(acetic acid-form)]. The column is washed with one liter of water. The eluate and washing are combined, treated with activated charcoal and then concentrated under reduced pressure. The residue is dissolved in 200 ml of ethanol, and the ethanol solution is concentrated under reduced pressure (these operations are repeated once more). The residue obtained is dissolved in ethanol. 58.6 g of ethanol hydrochloric acid (HCl-content: 30%) are added to the solution. Then, the mixture is concentrated under reduced pressure. The residue is again dissolved in 200 ml of ethanol, and the ethanol solution is concentrated. The oily residue thus obtained is dissolved in 200 ml of ethanol under heating. After cooling, the crystalline precipitates are collected by filtration and then recrystallized from methanol-acetone. 47.6 g of nicotinoyl carnitine amide chloride.HCl are obtained. M.p. 180°–181° C. Yield: 64.5%

EXPERIMENT I

Test compounds are administered orally to groups of 5 rats (body weight: about 290 g) which fasted overnight. Blood samples were collected from the tail vein at intervals. Blood free fatty acid, serum-triglyceride and serum-cholesterol were determined, respectively. The results are shown in Table 1.

Table 1

| Test Compounds (Dose) | Blood-free fatty acids ($\mu$ moles/dl) | | | | Serum triglyceride (mg/dl) | | Serum-cholesterol (mg/dl) | |
|---|---|---|---|---|---|---|---|---|
| | Period of time after the oral administration (hrs.) | | | | | | | |
| | 0 | 2 | 6 | 10 | 6 | 10 | 6 | 10 |
| A* (1 mmol/kg) | 52 ± 6 | 27 ± 1 | 29 ± 3 | 65 ± 6 | 12 ± 3 | 16 ± 4 | 55 ± 8 | 50 ± 7 |
| Nicotinic acid (1 mmol/kg) | 38 ± 2 | 22 ± 2 | 60 ;35 5 | 66 ± 12 | 22 ± 2 | 27 ± 3 | 74 ± 4 | 70 ± 4 |
| Control | 38 ± 1 | 40 ± 3 | 49 ± 4 | 53 ± 7 | 24 ± 1 | 37 ± 3 | 75 ± 4 | 76 ± 4 |

All the numerical values in the table show the mean values ± standard error.
*Nicotinoyl carnitine ethyl ester nitrate . HNO$_3$

EXPERIMENT II

Test compounds were administered orally to groups of 5 rats (body weight: about 170 g) which fasted overnight. Blood samples were collected from the tail vain at intervals, and serum-triglyceride was determined. The results are shown in Table 2.

Table 2

| Test compounds (Dose) | Serum-triglyceride (mg/dl) | |
|---|---|---|
| | Period of time after the oral administraton (hrs.) | |
| | 6 | 12 |
| B** (1 mmol/kg) | 13 ± 5 | 13 ± 4 |
| C*** (1 mmol/kg) | 10 ± 1 | 23 ± 3 |
| Nicotinic acid (1 mmol/kg) + Carnitine HCl (1 mmol/kg) | 28 ± 7 | 34 ± 5 |
| Control | 21 ± 3 | 19 ± 7 |

All the numerical values in the table show the mean values ± standard error.
**Nicotinoyl carnitine ethyl ester chloride. H$_2$O
***Nicotinoyl carnitine benzyl ester chloride

EXPERIMENT III

Test compounds were administered orally to ddY male mice or SD-strain male rats. Seventy-two hours after the administration, 50% lethal dose of the test compounds were estimated in accordance with Van der Waerden's Method. The results are shown in Table 3.

Table 3

|  | Acute toxicity $LD_{50}$, g/kg | |
|---|---|---|
|  | Test compounds | |
|  | B** | D**** |
| ddY-strain male mice | 5.9 | > 7.2 |
| SD-strain male rats | 6.9 | > 7.0 |

**Nicotinoyl carnitine ethyl ester chloride . $H_2O$
****Nicotinoyl carnitine amide chloride . HCl

What we claim is:
1. A compound of the formula:

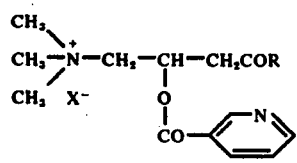

wherein R is lower alkoxy, benzyloxy or amino and X is an anionic residue of a pharmaceutically acceptable acid, or a pharmaceutically acceptable acid addition salt of said compound.

2. The compound claimed in claim 1, in which R is lower alkoxy.
3. The compound claimed in claim 1, in which R is benzyloxy.
4. The compound claimed in claim 1, in which R is amino.
5. The compound claimed in claim 1, in which R is methyl, ethyl, butyl or benzyloxy, and X is an ion selected from the group consisting of halide, nitrate, sulfate, phosphate, chlorate, bromate, lower alkane-monocarboxylate, lower alkene-dicarboxylate, lower alkane-dicarboxylate, lower alkyl-sulfonate, benzenesulfonate and toluenesulfonate.

6. Nicotinoyl carnitine ethyl ester nitrate.$HNO_3$.
7. Nicotinoyl carnitine ethyl ester phosphate.
8. Nicotinoyl carnitine ethyl ester chloride.
9. Nicotinoyl carnitine ethyl ester chloride.HCl.
10. The compound claimed in claim 1, in which R is methoxy, ethoxy, butoxy or benzyloxy.
11. A therapeutic composition, useful as a hypolipidemic agent, which comprises a therapeutically effective amount of a compound of the formula:

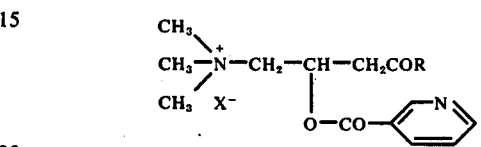

wherein R is lower alkoxy, benzyloxy or amino and X is an anionic residue of a pharmaceutically acceptable acid, or a pharmaceutically acceptable acid addition salt of said compound, and a pharmaceutically acceptable carrier therefor.

12. The composition of claim 10 wherein said therapeutic amount is that which is necessary to produce a hypolipidemic effect by administration to a warm-blooded animal.
13. The composition of claim 10 wherein said therapeutic amount for an adult patient is 200 mg to 10 g per day.

* * * * *